(12) United States Patent  (10) Patent No.: US 8,936,575 B2
Moulton  (45) Date of Patent: Jan. 20, 2015

(54) CANNULA-TIP SHIELDING MECHANISM

(75) Inventor: William G. Moulton, West Jordan, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 12/407,182

(22) Filed: Mar. 19, 2009

(65) Prior Publication Data

US 2010/0241087 A1   Sep. 23, 2010

(51) Int. Cl.
*A61M 5/178* (2006.01)
*A61M 25/06* (2006.01)
*A61M 5/32* (2006.01)

(52) U.S. Cl.
CPC ....... *A61M 25/0618* (2013.01); *A61M 25/0612* (2013.01); *A61M 5/3273* (2013.01); *A61M 2005/3226* (2013.01)
USPC ............ 604/164.01; 604/164.08; 604/165.01; 604/171

(58) Field of Classification Search
CPC ...................... A61M 25/0618; A61M 25/0625
USPC .......... 604/164.01, 164.08, 165.01, 171, 110, 604/500, 506
See application file for complete search history.

(56) References Cited

U.S. PATENT DOCUMENTS

| | | | |
|---|---|---|---|
| 4,511,359 A | * | 4/1985 | Vaillancourt ................. 604/411 |
| 4,952,207 A | * | 8/1990 | Lemieux ........................ 604/164 |
| 4,964,854 A | | 10/1990 | Luther |
| 5,085,648 A | | 2/1992 | Purdy et al. |
| 5,135,504 A | | 8/1992 | McLees |
| 5,601,536 A | | 2/1997 | Crawford et al. |
| 5,833,670 A | | 11/1998 | Dillon et al. |
| 6,004,294 A | | 12/1999 | Brimhall et al. |
| 6,012,213 A | | 1/2000 | Chang et al. |
| 6,117,108 A | | 9/2000 | Woehr et al. |
| 6,224,569 B1 | | 5/2001 | Brimhall |
| 6,287,278 B1 | | 9/2001 | Woehr et al. |
| 6,322,537 B1 | | 11/2001 | Chang |
| 6,379,333 B1 | | 4/2002 | Brimhall et al. |

(Continued)

FOREIGN PATENT DOCUMENTS

| | | |
|---|---|---|
| EP | 1 306 097 A1 | 5/2003 |
| JP | 07-148270 | 6/1995 |

(Continued)

*Primary Examiner* — Edelmira Bosques
(74) *Attorney, Agent, or Firm* — Jeanne Lukasavage; Craig Metcalf; Kirton McConkie (57) ABSTRACT

A needle tip shielding mechanism is described herein. The shielding mechanism comprises an outer housing, an inner housing, and a needle having a needle feature. Generally, the outer housing comprises at least one adapter-interlock feature. Moreover, the inner housing comprises a needle-feature capture mechanism, such as a washer feature, and a needle-tip capture mechanism, such as duckbilled tip barrier. In some cases, the inner housing is slidably moveable within the outer housing. In such cases, the inner housing is movable between a first position that biases the adapter-interlock feature into an engaged position and a second position that allows the adapter-interlock feature to move to an unengaged position. This ability to bias the interlock feature in the engaged position and to allow the interlock feature to move to the unengaged position allows the shielding mechanism to be selectively coupled to and released from an interlock-feature mating component within a catheter adapter.

19 Claims, 10 Drawing Sheets

(56) References Cited

U.S. PATENT DOCUMENTS

| | | |
|---|---|---|
| 6,443,927 B1 | 9/2002 | Cook |
| 6,443,929 B1 | 9/2002 | Kuracina et al. |
| 6,616,630 B1 | 9/2003 | Woehr et al. |
| 6,629,959 B2 | 10/2003 | Kuracina et al. |
| 6,652,486 B2 | 11/2003 | Bialecki et al. |
| 6,652,490 B2 | 11/2003 | Howell |
| 6,663,592 B2 | 12/2003 | Rhad et al. |
| 6,692,471 B2 | 2/2004 | Boudreaux |
| 6,761,706 B2 | 7/2004 | Vaillancourt |
| 6,860,871 B2 | 3/2005 | Kuracina et al. |
| 6,914,212 B2 | 7/2005 | Adams |
| 7,002,098 B2 | 2/2006 | Adams |
| 7,160,269 B2 | 1/2007 | Woehr |
| 7,186,239 B2 | 3/2007 | Woehr |
| 7,214,208 B2 | 5/2007 | Vaillancourt |
| 7,238,169 B2 | 7/2007 | Takagi et al. |
| 7,264,613 B2 | 9/2007 | Woehr et al. |
| 8,496,623 B2 * | 7/2013 | Burkholz .................. 604/164.08 |
| 2002/0169418 A1 | 11/2002 | Menzi et al. |
| 2003/0144627 A1 | 7/2003 | Woehr et al. |
| 2004/0010227 A1 | 1/2004 | Riesenberger et al. |
| 2004/0186434 A1 | 9/2004 | Harding et al. |
| 2004/0204681 A1 | 10/2004 | Thoresen et al. |
| 2004/0225260 A1 | 11/2004 | Villa et al. |
| 2004/0236288 A1 * | 11/2004 | Howell et al. .................. 604/263 |
| 2004/0243061 A1 | 12/2004 | McGurk |
| 2005/0027263 A1 | 2/2005 | Woehr et al. |
| 2005/0080378 A1 | 4/2005 | Cindrich et al. |
| 2006/0116638 A1 | 6/2006 | Woehr et al. |
| 2006/0270980 A1 | 11/2006 | Menzi et al. |
| 2007/0100297 A1 | 5/2007 | Woehr et al. |
| 2007/0112305 A1 * | 5/2007 | Brimhall .................. 604/164.08 |
| 2007/0129689 A1 | 6/2007 | Woehr et al. |
| 2007/0156093 A1 | 7/2007 | Woehr |
| 2007/0179446 A1 | 8/2007 | Carrez et al. |
| 2007/0179447 A1 | 8/2007 | Carrez et al. |

FOREIGN PATENT DOCUMENTS

| | | |
|---|---|---|
| JP | 2006-522646 A | 10/2006 |
| WO | 2006/062983 A1 | 6/2006 |
| WO | 2008/021132 A1 | 2/2008 |

* cited by examiner

CANNULA-TIP SHIELDING MECHANISM

BACKGROUND OF THE INVENTION

This invention relates generally to vascular access devices and associated methods. More specifically, this invention relates to a needle-tip shielding mechanism having an interlock system that allows the shielding mechanism to be selectively coupled to a catheter adapter. The interlock system also allows the shielding mechanism to be selectively released and removed from the adapter with little to no friction between the interlock system and the adapter.

Generally, vascular access devices are used for communicating fluid with the vascular system of patients. For example, catheters are used for infusing fluid (e.g., saline solution, medicaments, and/or total parenteral nutrition) into a patient, withdrawing fluids (e.g., blood) from a patient, and/or monitoring various parameters of the patient's vascular system.

Intravenous (IV) catheter assemblies are among the various types of vascular access devices. Over-the-needle peripheral IV catheters are a common IV catheter configuration. As its name implies, an over-the-needle catheter is mounted over an introducer needle having a sharp distal tip. The introducer needle is generally a hypodermic needle coupled to a needle assembly to help guide the needle and to facilitate its cooperation with the catheter. At least the inner surface of the distal portion of the catheter tightly engages the outer surface of the needle to prevent peelback of the catheter and, thereby, facilitate insertion of the catheter into the blood vessel. The catheter and the introducer needle are often assembled so that the distal tip of the introducer needle extends beyond the distal tip of the catheter. Moreover, the catheter and the needle are often assembled so that, during insertion, the bevel of the needle faces up, away from the patient's skin. The catheter and introducer needle are generally inserted at a shallow angle through the patient's skin into a blood vessel.

In order to verify proper placement of the needle and/or the catheter within the blood vessel, an operator of catheter assembly often confirms that there is a "flashback" of blood into a flashback chamber associated with the needle assembly. Flashback generally entails the appearance of a small amount of blood, which is visible within the needle assembly or between the needle and the catheter. Once proper placement of the distal tip of the catheter in the blood vessel is confirmed, the operator may apply pressure to the blood vessel by pressing down on the patient's skin over the blood vessel, distal to the needle and the catheter. This finger pressure momentarily occludes the vessel, minimizing further blood flow through the needle and the catheter.

The operator may then withdraw the introducer needle from the catheter. The needle may be withdrawn into a needle tip cover that extends over the needle's tip and prevents accidental needle sticks. In general, a needle tip cover includes a sleeve or other similar device that is designed to trap/capture the needle tip when the introducer needle is withdrawn from the catheter and the patient. After the needle is withdrawn, the catheter is left in place to provide intravenous access to the patient.

The separation of the introducer needle assembly from the catheter portions of the catheter assembly presents numerous potential hazards to the operator and others in the area. Indeed, as indicated above, there is a risk of accidental needle sticks if the needle tip is not secured properly in a needle tip cover. Additionally, because the needle tip shield is often frictionally engaged within a catheter adapter, an operator may need to jerk or forcefully pull the needle tip shield from the catheter adapter. This jerking and pulling movement may cause discomfort to the patient.

Furthermore, because the needle has been in contact with blood in the patient's vasculature, blood is often present on the needle's exterior as well as inside the lumen of the needle. As the needle is withdrawn from the catheter, there is a risk that this blood will drip from the needle tip or come into contact with other surfaces to expose people and equipment to blood.

The present invention relates to a needle-tip shielding mechanism that allows a needle with a needle feature to be retracted from an unshielded position and be trapped in a shielded position. Additionally, the shielding mechanism is adapted to be removed from a catheter adapter with little to no friction. Accordingly, the described shielding mechanism is configured to significantly limit or prevent accidental needle sticks, to be easily removed from a catheter assembly, and to reduce blood exposure.

BRIEF SUMMARY OF THE INVENTION

The present invention relates to a needle-tip shielding mechanism that is designed to overcome some of the limitations known in the art. Typically, the shielding mechanism comprises a needle, an inner housing, an outer housing, and a catheter adapter.

The needle may comprise any needle or cannula that can be used with the described shielding mechanism. For instance, the needle can comprise a hypodermic needle, such as an IV catheter introducer needle. Additionally, the needle may comprise any component or characteristic that allows it to be used with, and be captured by, the described shielding mechanism. In one example, the needle comprises a needle feature, such as a crimp feature, a welded ferrule feature, a notched crimp feature, or another needle feature that has a surface that extends laterally past the outer diameter ("OD") of the needle.

The inner housing may comprise any component or characteristic that allows it to capture the needle tip in a manner that limits the proximal and distal movement of the needle when the needle is in a shielded position. In one example, the inner housing comprises an interior space through which the needle extends axially.

In another example, the inner housing comprises a needle-feature capture mechanism. While the needle-feature capture mechanism may comprise any component that limits the proximal movement of the needle feature within the inner housing, in some instances, the needle-feature capture mechanism comprises a needle through hole. In such instances, the needle through hole is sized and shaped to allow the needle, but not the laterally extending surface of the needle feature, to pass therethrough.

In still another example, the inner housing comprises a needle-tip capture mechanism. While the needle-tip capture mechanism may comprise any suitable component that limits the needle's distal movement when the needle is in the shielded position, in some embodiments, the needle-tip capture mechanism comprises a duckbilled tip barrier. In such embodiments, the duckbilled tip barrier may have any suitable characteristic. In one example, the tip barrier comprises at least one flap that extends proximally into the inner housing. In this example, at least a portion of each flap extends at an acute angle from an interior surface of the inner housing. In this example, each flap is also biased away from the interior surface from which the flap originates. Accordingly, when the needle is in the unshielded position, each flap is biased against the needle. Furthermore, when the needle tip is retracted proximally past a proximal-most end of the flaps, the flaps move to a position that blocks the needle tip from forward movement, preventing it from reemerging distally from the inner housing.

The outer housing may comprise virtually any suitable component or characteristic that allows the inner housing to translate or slide within the outer housing, while still allowing the shielding mechanism to be used as intended. In one example, the outer housing comprises a canister that is sized and shaped to slidably receive the inner housing in a manner that allows the inner housing to translate between a distal position and a proximal position within the outer housing. In another example, the outer housing comprises a proximal stop that prevents the inner housing from moving proximally past a certain point with respect to the outer housing. In still another example, the proximal end of the outer housing comprises a proximal opening through which the needle extends.

In yet another example, the outer housing comprises an interlock system that allows the outer housing to be selectively and removably coupled to a catheter adapter. For instance, the outer housing can comprise at least one adapter-interlock feature. In such instances, the interlock feature may be moved into, or from, an engaged position in any suitable manner. Indeed, in some instances, when the inner housing is in the distal position, the inner housing biases the interlock features radially outward into the engaged position. Conversely, in such instances, when the inner housing is moved to the proximal position, the interlock feature is allowed to move radially inward, to an unengaged position.

The adapter-interlock features may comprise any characteristic that allows them to act as intended. In one example, the interlock feature comprises an arm that is pivotally attached to the outer housing. In this example, the arm may be pivotally attached to the outer housing in any suitable manner (e.g., through a notch or perforation between the arm and the outer housing). In another example, the interlock features each comprise a frictional engagement (e.g., a barb, an undercut, etc.) that is adapted to frictionally/mechanically engage a corresponding surface within the lumen of the catheter adapter.

In addition to the aforementioned characteristics, the shielding mechanism may comprise any suitable component or characteristic that allows the mechanism to function as intended. In some instances, the shielding mechanism comprises means for biasing the inner housing into the distal position. In one example of such biasing means, the biasing means comprises an inner-housing detent mechanism that biases the inner housing in the distal position, once the inner housing has been moved to the distal position. For instance, the detent mechanism may comprise protuberance that catches/engages a portion of the inner housing (e.g., the proximal end of the inner housing), once the inner housing has been moved to the distal position. In such instances, a slight pull in the proximal direction can release the detent mechanism and allow the inner housing to move to the proximal position.

In another example of biasing means, the proximal opening of the outer shield is enlarged to allow a protuberant feature on the needle or a needle hub to communicate with the inner shield. In this example, the shielding mechanism can be inserted into the inner lumen of the catheter adapter with the inner housing disposed in the proximal position. Once the outer housing is placed in its proper position, the needle can be pushed distally so that the protuberant feature on the needle/needle hub communicates with the inner housing and pushes the inner housing into the distal position so the interlock features are forced into the engaged position.

The shielding mechanism may function in any suitable manner. In one example, before use, the needle is in the unshielded position and the inner housing is disposed in the distal position. To shield the needle tip, the needle is pulled proximally with respect to the inner housing. As the needle moves proximally, the force (e.g., friction) between the inner housing and the outer housing remains higher than the force between the inner housing and the needle until the needle feature contacts the needle-feature capture mechanism. In other words, until the needle feature contacts the needle-feature capture mechanism, the inner housing remains in the distal position.

Once the needle feature contacts the needle-feature capture mechanism and the needle continues to be pulled proximally, the force between the needle and the inner housing becomes greater than the force between the inner housing and the outer housing. Accordingly, the proximal force on the needle causes the inner housing to translate proximally with respect to the outer housing. Once the inner housing is moved to the proximal position, the interlock features are allowed to move to the unengaged position. When the interlock features are released from the engaged position, the shielding mechanism can be extracted from the catheter adapter with little to no friction between interlock features and the interior surface of the adapter. Moreover, with the needle tip trapped within the inner housing and the outer housing uncoupled from the catheter adapter, the needle and shielding mechanism can be disposed of safely.

BRIEF DESCRIPTION OF THE SEVERAL VIEWS OF THE FIGURES

In order that the manner in which the above-recited and other features and advantages of the invention will be readily understood, a more particular description of the needle-tip shielding mechanism briefly described above will be rendered by reference to specific embodiments thereof, which are illustrated in the appended Figures. Understanding that these Figures depict only typical embodiments and are not, therefore, to be considered to be limiting of its scope, the invention will be described and explained with additional specificity and detail through the use of the accompanying Figures in which.

DETAILED DESCRIPTION OF THE INVENTION

The presently preferred embodiments of the described invention will be best understood by reference to the Figures, wherein like parts are designated by like numerals throughout. It will be readily understood that the components of the present invention, as generally described and illustrated in the Figures herein, could be arranged and designed in a wide variety of different configurations. Thus, the following more detailed description of the embodiments of the needle-tip shielding mechanism, as represented in FIGS. 1 through 9, is not intended to limit the scope of the invention, as claimed, but is merely representative of some presently preferred embodiments of the invention.

The present invention relates to a needle-tip shielding mechanism. Generally, the shielding mechanism allows the needle to be moved from an unshielded position in which the needle tip is exposed from the shielding mechanism, to a shielded position in which the needle tip is both covered by the shielding mechanism and is prevented from emerging from a distal and a proximal end of the mechanism. Additionally, the shielding mechanism comprises an interlock system that allows the shielding mechanism to be selectively coupled to a catheter adapter. In some embodiments, the interlock system further allows the shielding mechanism to be selectively uncoupled and removed from the adapter with little to no friction between the interlock system and the adapter.

Figure 1:
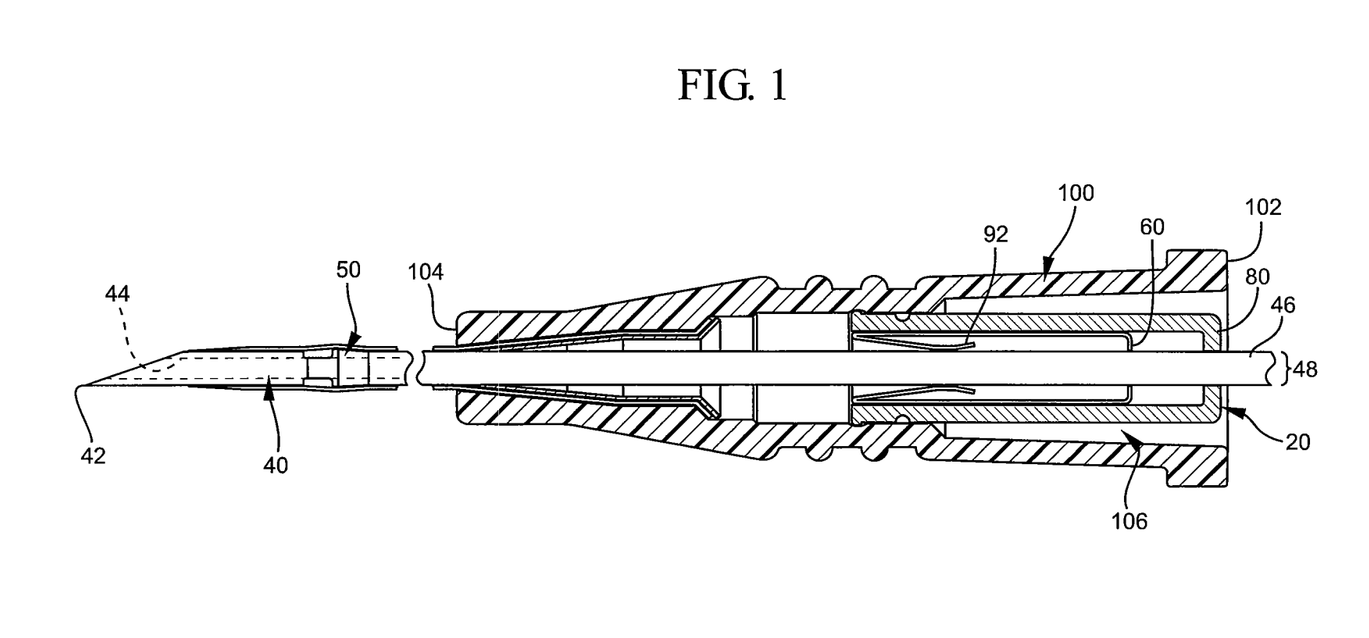
FIG. 1 illustrates a cross section view of a representative embodiment of a catheter adapter comprising a needle-tip shielding mechanism in which a needle is disposed in an unshielded position.

The shielding mechanism can comprise any component or characteristic that allows it to both trap a needle in the shielded position and to selectively couple and uncouple from a catheter adapter. For example, FIG. 1 shows a representative embodiment in which the needle-tip shielding mechanism 20 comprises an inner housing 60, and an outer housing 80. The shielding mechanism operates in conjunction with a needle 40. Additionally, FIG. 1 illustrates that the shielding mechanism 20 can be selectively coupled with a catheter adapter 100. To provide a better understanding of the shielding mechanism, the catheter adapter, needle, inner housing, and outer housing are each described below in further detail.

The shielding mechanism may be used with any suitable catheter adapter, including a catheter adapter for an over-the-needle peripheral IV catheter assembly. Furthermore, the catheter adapter may comprise any suitable component. By way of example, FIG. 1 shows the catheter adapter 100 comprises a proximal end 102 and a distal end 104 with an inner lumen 106 extending between the two. FIG. 1 also shows that the proximal end 102 of the adapter 100 is configured to receive the shielding mechanism 20 so the outer housing 80 can be coupled within the adapter's lumen 106.

As mentioned above, the shielding mechanism 20 operates in conjunction with a needle (e.g., needle 40). As used herein, the terms "needle" or "needles" may refer to virtually any rigid cannula, tube, solid needle (e.g., a trocar), etc. having a sharpened distal tip that is configured to puncture and be inserted into a patient's body. Some examples of such needles comprise hypodermic needles, trocars, and cannulae that may expose their operator to the risk of unintended needle-sticking injuries or blood exposure.

The needle may comprise any suitable type of hypodermic needle, including an introducer needle for use in an IV catheter assembly (e.g., an over-the-needle peripheral IV catheter assembly). Indeed, according to some presently preferred embodiments, FIG. 1 shows the needle comprises an introducer needle 40.

The introducer needle may have any characteristic that is suitable for use with an IV catheter assembly. By way of illustration, FIG. 1 shows an embodiment in which the introducer needle 40 comprises a sharpened distal tip 42, an inner lumen 44, an elongated tubular portion 46 with a substantially constant outer diameter ("OD") 48, and a needle feature 50.

Each of the introducer needle's aforementioned components may comprise any suitable characteristic. In one example, the distal tip of the needle is selected from a standard bevel, a short bevel, a true short bevel, a bias grind point, a vet point, a lancet point, a deflected point (anti-coring), and another suitable needle point. In another example, the needle's lumen and elongated tubular portion can be any suitable size. For instance, the needle may be any length or gauge (e.g., from a 7 to a 33 on the Stubs scale) that allows it to be used as the introducer needle in an IV assembly.

Figure 2A:
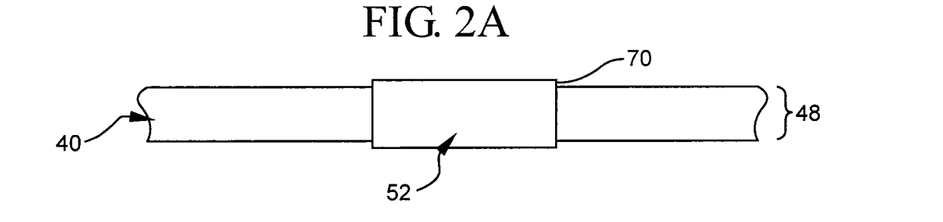
FIGS. 2A-2D each illustrate a plan view of a representative embodiment of a needle feature.
Figure 2B:
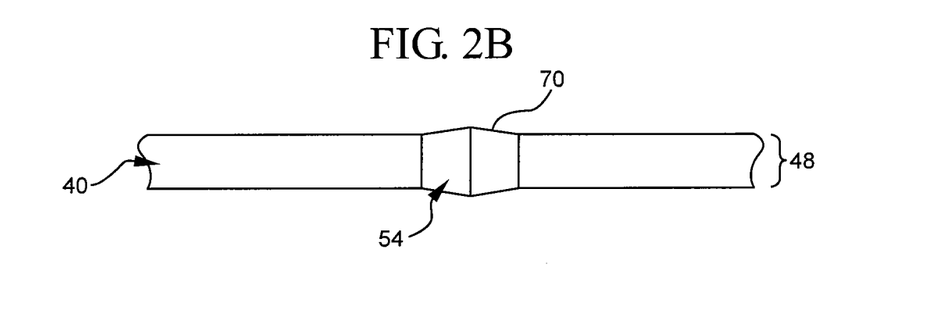
Figure 2C:
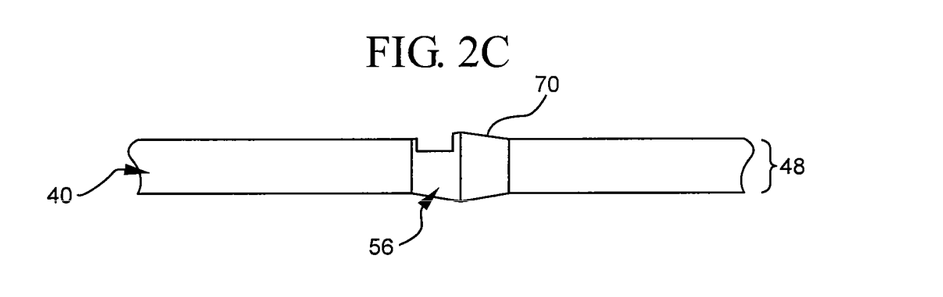
Figure 2D:
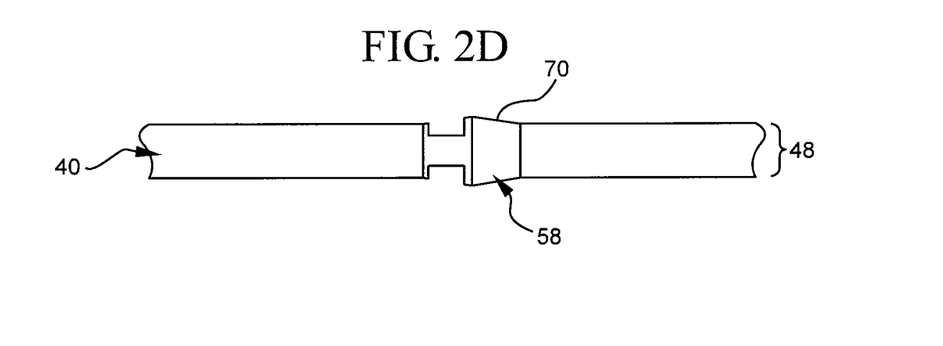

In still another example, the needle feature 50 may comprise any suitable object on the needle that is capable of being captured in the inner housing (as described below) in a manner that restricts the feature's proximal movement with respect to the inner housing. For instance, the needle feature may comprise any surface on the needle that extends laterally past needle's OD and which is adapted to limit the needle's proximal movement with respect to the inner housing. By way of example, FIGS. 2A through 2D illustrate several examples of suitable needle features. Specifically, FIG. 2A shows a representative embodiment of a needle 40 in which the needle feature comprises a ferrule 52. FIG. 2B shows another representative embodiment in which the needle feature comprises a crimp feature 54. FIGS. 2C and 2D show additional embodiments in which the needle feature comprises a crimp with a single notch 56 and a plurality of notches 58, respectively.

Regardless of the specific type of needle feature, the needle feature may have any suitable characteristic. For instance, the feature may be any suitable shape or size. Similarly, the needle feature may include any component that allows the needle to function as intended and limits the needle's proximal movement with respect to the inner housing. For instance, FIGS. 2A through 2D show that the various needle features (e.g., 52, 54, 56, and 58) comprise a proximal engagement 70, or a proximal surface that extends laterally past the needle's OD 48.

Figure 3:
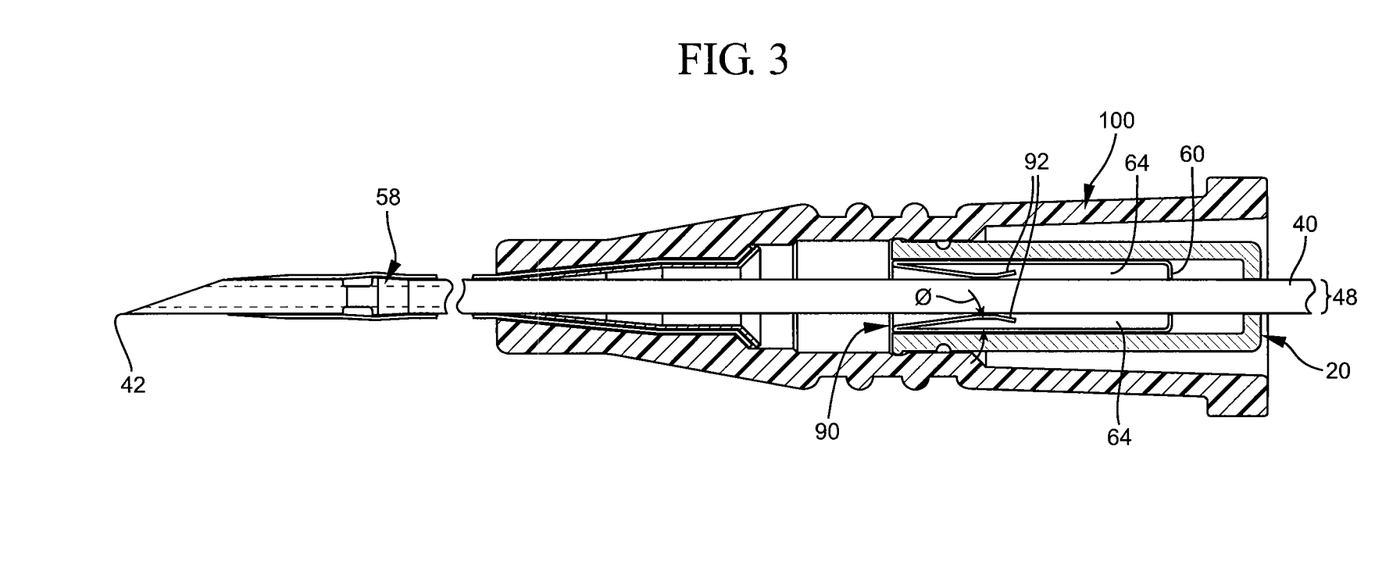
FIG. 3 illustrates a cross section view of a representative embodiment of the needle-tip shielding mechanism in which the needle tip is in an unshielded position.

As previously mentioned, the shielding mechanism also comprises an inner housing. The inner housing may comprise any suitable characteristic that allows it to capture and shield the needle tip as well as to translate proximally and/or distally within the outer housing (described below). In one example of a suitable characteristic, the inner housing can be any suitable size and have any suitable shape through which the needle may pass axially. For instance, the inner housing can be shorter than the outer housing and have an outer diameter that allows the inner housing to slide within the outer housing. In other instances, the inner housing can be substantially cylindrical, cuboidal, tubular, cage-like, irregular, or have any other suitable shape. By way of illustration, FIG. 3 shows a cross section view of a representative embodiment in which the outer surface of the inner housing 60 has a substantially cylindrical shape.

The inner housing may also have any suitable component that allows it to trap the needle's sharpened distal tip in a manner that prevents the needle tip from being exposed from either a proximal or a distal end of the inner housing. In one example, the inner housing comprises a needle-tip capture mechanism that limits the needle tip's distal movement once the needle has been moved to the shielded position. In another example, the inner housing comprises a needle-feature capture mechanism that acts to capture the needle feature and limit the needle feature's proximal movement when the needle is in the shielded position. In still another example, the inner housing comprises both a needle-tip and a needle-feature capture mechanism.

The needle-tip capture mechanism may comprise any component that captures the needle's tip and limits the tip's distal movement once the needle has been moved to the shielded position. Some examples of suitable needle-tip capture mechanisms include a needle tip barrier, such as a duckbilled tip barrier, a conventional transverse tip barrier, or another component that is configured to capture the needle's tip and prevent the tip from reemerging distally from the inner housing after the tip has been moved to the shielded position.

In some presently preferred embodiments, the needle-tip capture mechanism comprises a duckbilled tip barrier. In such embodiments, the duckbilled tip barrier may comprise any component or characteristic that allows it to prevent the needle tip from reemerging from the inner housing. In one example, the duckbilled tip barrier comprises at least one flap that extends proximally into the inner housing. For instance, FIG. 3 shows an embodiment in which the duckbilled tip barrier 90 comprises two flaps 92.

The flaps can have any suitable characteristic that allows them to limit the needle tip's distal movement after the needle is moved to the shielded position. In one example, FIG. 3 shows that at least a portion of each flap 92 extends away from an interior surface 64 of the inner housing 60, from which the flap 92 originates, at an acute angle θ.

In another example, each flap is biased away from the interior surface of the inner housing from which the flap originates. For instance, FIG. 3 shows that when the needle 40 is in the unshielded position, each flap 92 is biased away from the interior surface 64 from which it originates towards the needle 40. Furthermore, FIGS. 4A and 4B, which respectively illustrate a top plan and a side plan cutaway view of the shielding mechanism 20, show that once the needle tip 42 is pulled proximally past a proximal-most end 94 of the flaps 92, the flaps 92 are allowed to bias against each other in a manner that blocks the needle tip 42 and prevents it from being moved distally out of the inner housing 60.

Figure 4A:
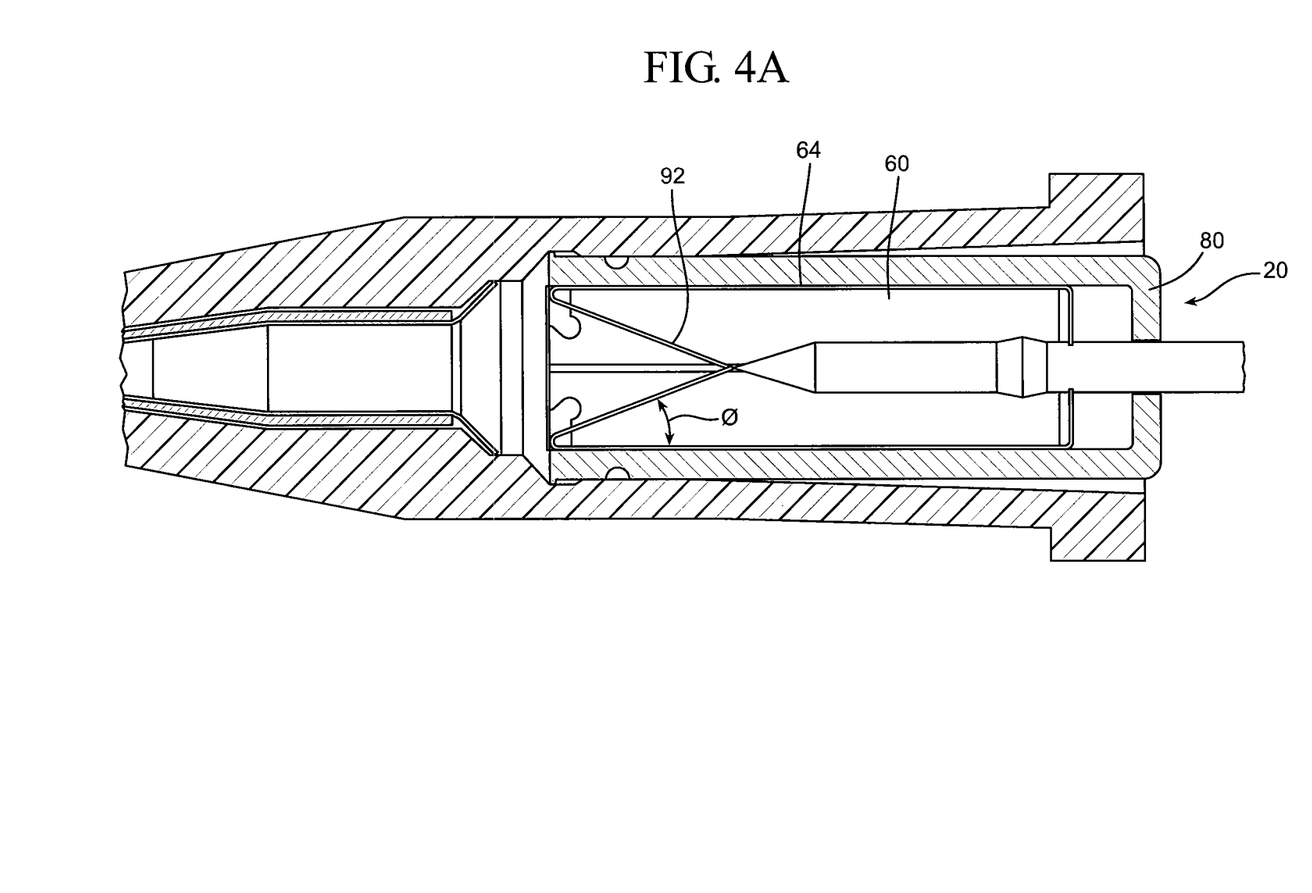
FIG. 4A illustrates a cutaway top plan view of a representative embodiment of the needle-tip shielding mechanism in which the needle tip is in the shielded position.
Figure 4B:
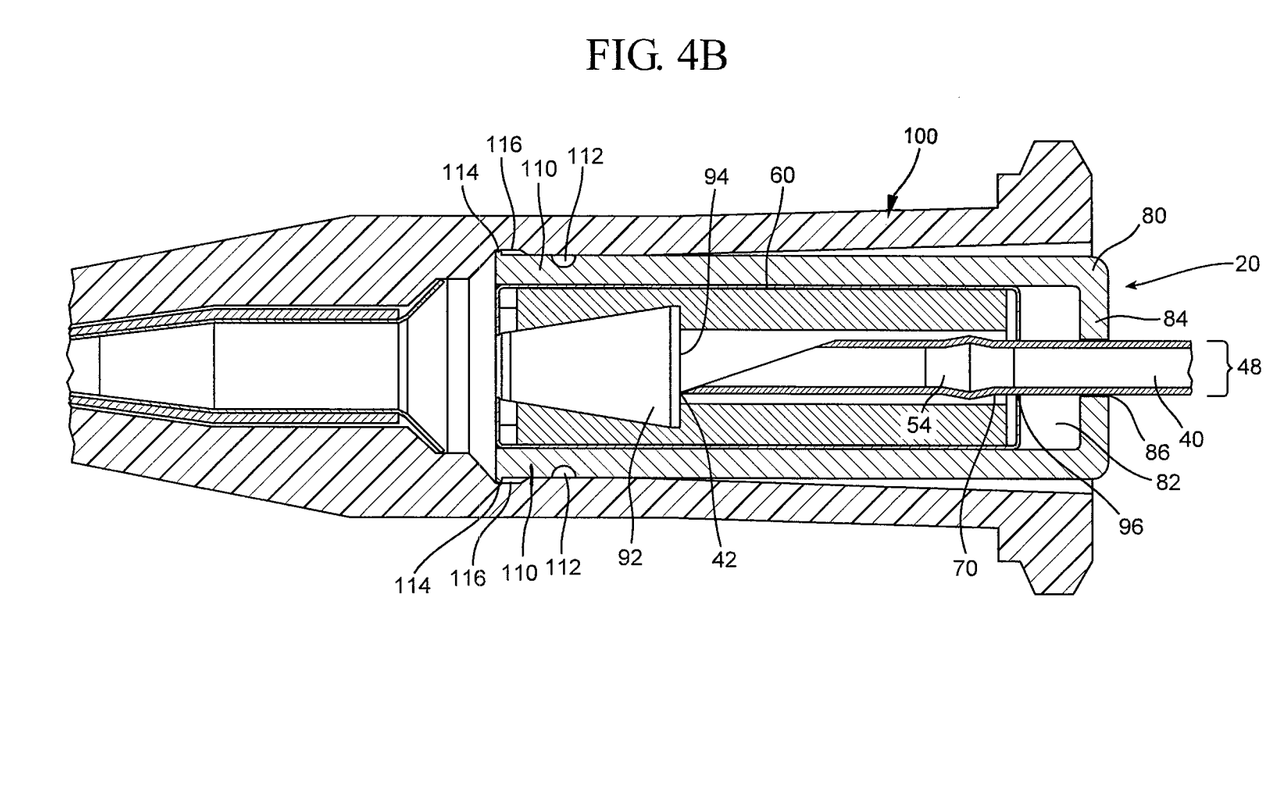
FIG. 4B illustrates a cutaway side plan view of a representative embodiment of the needle-tip shielding mechanism in which the needle tip is in the shielded position and an inner housing is disposed in a distal position within an outer housing in a manner that biases a plurality of adapter-interlock features into an engaged position.

In still another example of a suitable flap characteristic, FIG. 4B illustrates that the proximal end 94 of one or more flaps 92 is broad enough to extend laterally past the OD 48 of the needle 40. In this example, the flaps can prevent the needle from circumventing the flaps when the needle is twisted.

Where the inner housing comprises a needle-feature capture mechanism, the feature capture mechanism may comprise any suitable component or characteristic that allows the capture mechanism to limit the needle feature's proximal movement with respect to the inner housing. For example, the needle-feature capture mechanism may comprise a needle through hole (e.g., a conventional washer feature) or any other suitable surface that is adapted to contact the proximal engagement of the needle feature and prevent the needle feature from moving proximally past that surface. For instance, FIG. 4B shows a representative embodiment in which the needle-feature capture mechanism comprises a needle through hole 96 that is sized and shaped to allow the needle 40, but not the proximal engagement 70 of the needle feature 54, to pass therethrough.

Where the needle-feature capture mechanism comprises a needle through hole, the port may have any suitable characteristic. In one example, the needle through hole is configured to wipe or squeegee fluids (e.g., blood) from the OD of the needle as the needle is pulled proximally through the needle through hole. Accordingly, the inner housing may further reduce the risk of blood exposure. Additionally, this squeegee effect may be provided in any suitable manner. For instance, the needle through hole may comprise a rubber, plastic, elastomeric, or other similar ring that is capable of wiping blood from the needle.

Figure 5:
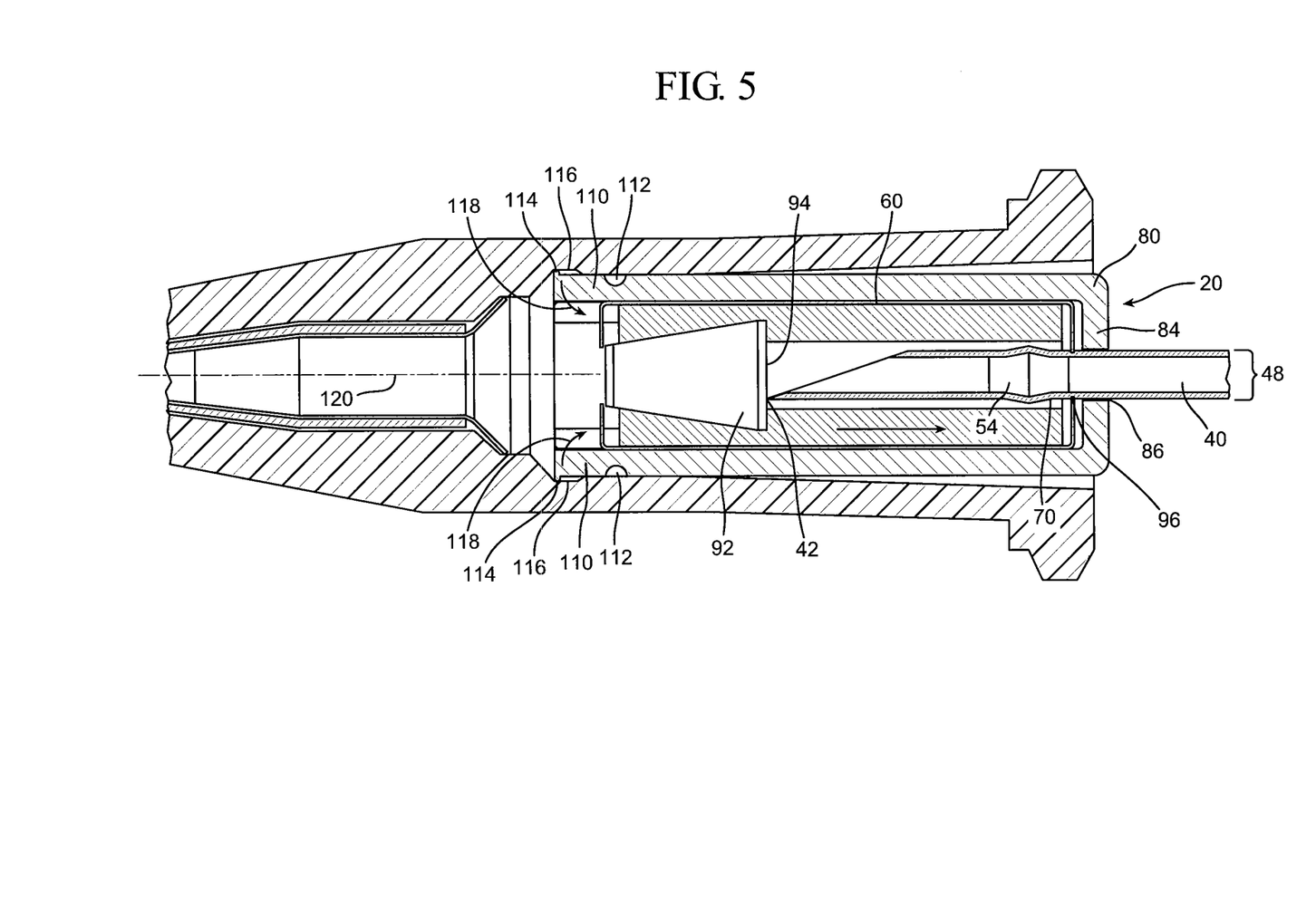
FIG. 5 illustrates a cutaway side plan view of a representative embodiment of the needle-tip shielding mechanism in which the needle tip is in the shielded position and the inner housing is disposed in a proximal position within the outer housing so that the plurality of adapter-interlock features are released from the engaged position.

As previously stated, the shielding mechanism further comprises an outer housing. The outer housing may have any suitable component or characteristic that allows the inner housing to translate within the outer housing and which also allows the outer housing to be selectively and releasably coupled to a catheter adapter. In one example, FIG. 4B shows the outer housing 80 comprises a sleeve with an inner space 82 that is sized and shaped to allow the inner housing 60 to translate between a distal position (as shown in FIG. 4B) and a proximal position (as shown in FIG. 5) within the outer housing 80. In another example, FIG. 4B shows the outer housing 80 comprises a proximal stop 84, or any suitable surface that prevents inner housing 60 from being removed proximally from the outer housing 80. In still another example, FIG. 4B shows an embodiment in which the outer housing 80 comprises a proximal opening 86 through which the needle 40 extends.

In yet another example, the outer housing can comprise any component or characteristic that allows outer housing to be selectively coupled to and uncoupled from a catheter adapter (discussed below). Indeed, in some presently preferred embodiments, the outer housing comprises an adapter-interlock feature. Moreover, in such embodiments, the outer housing may comprise any suitable number of interlock features, including, but not limited to, 1, 2, 3, 4, 5, 6, or more. For instance, FIG. 4B shows a representative embodiment in which the outer housing comprises 2 adapter-interlock features 110.

The adapter-interlock feature(s) may comprise any characteristic that allows them to selectively couple and uncouple the shielding mechanism from a catheter adapter. In one example, each adapter-interlock feature comprises an arm that is pivotally attached to the outer housing (i.e., extending as a cantilever from the housing). In this example, each arm may be pivotally attached to the outer housing in any suitable manner, including through the use of a notch, a hinge, a perforated edge, or any other connection between the interlock feature and the outer housing that allows the interlock feature to pivot with respect to the outer housing. By way of illustration, FIG. 4B illustrates an embodiment in which a notch 112 pivotally connects the arm 110 to the outer housing 80.

In still another example, one or more of the adapter-interlock features comprises a frictional engagement that is configured to frictionally or mechanically engage a corresponding surface within an inner lumen of a catheter adapter. Some examples of suitable frictional engagements comprise one or more protuberances, barbs, undercuts, and the like. By way of illustration, FIG. 4B shows an embodiment in which the interlock features 110 comprise a protuberance 114 that fits into interlock-feature mating component (e.g., undercut 116) within the catheter adapter 100.

The adapter-interlock features may function in any suitable manner. In one example, the adapter-interlock features articulate with the inner housing to form an interlock system. In this example, the interlock system may function in any suitable manner. For instance, the interlock features may be moved into an engaged position in any suitable manner. As used herein, the term engaged position may refer to a position in which the interlock features would couple the outer housing to a catheter adapter if the outer housing were properly seated in the adapter.

In one example of how the interlock features may be moved to the engaged position, FIG. 4B shows that when the inner housing 60 is in the distal position, the inner housing 60 biases the interlock features 110 radially outward into the engaged position. As used herein, the term distal position may refer to any position in which the inner housing is disposed in a location that biases the interlock features radially outward to the engaged position.

The adapter-interlock features may be released from the engaged position in any suitable manner. For instance, FIG. 5 shows a representative embodiment in which the interlock features 110 are released from the engaged position into an unengaged position (as represented by the arrows 118) when the inner housing 60 is moved to the proximal position. As used herein, the term proximal position may refer to any position in which the inner housing is located in a position that allows the interlock features to pivot in towards a longitudinal axis (e.g., axis 120) of the outer housing.

In addition to the aforementioned components and characteristics, the described shielding mechanism may comprise any additional component or characteristic that allows the mechanism to fulfill its intended purposes. For example, the needle can comprise a conventional notch for flashback confirmation.

Figure 6:
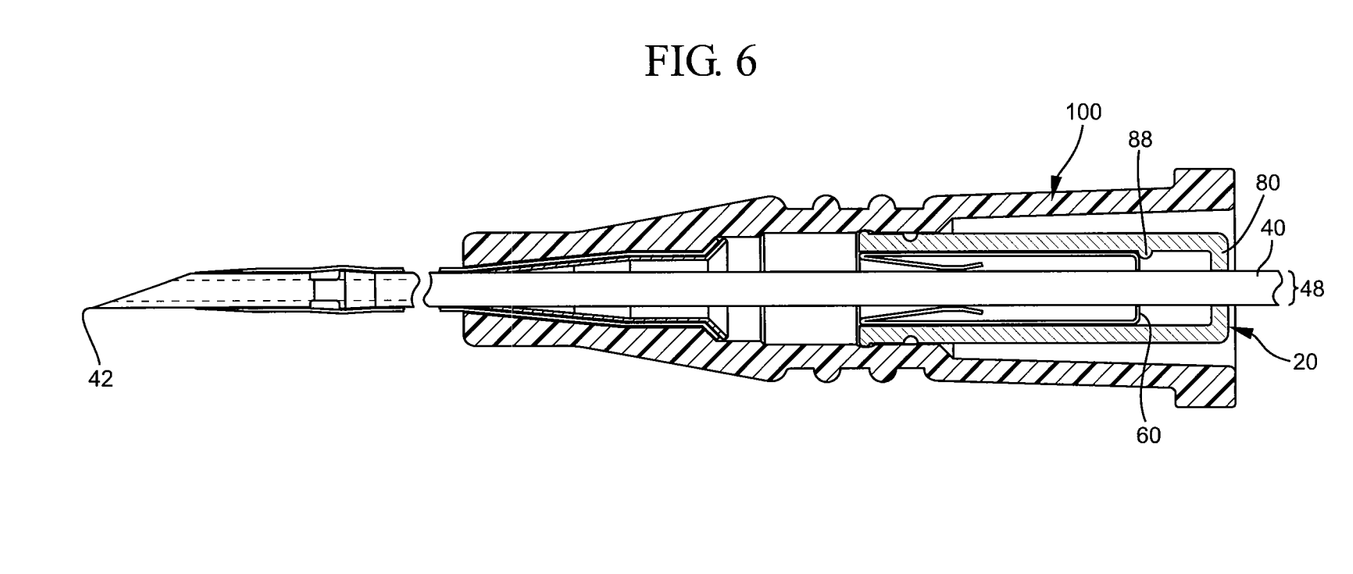
FIGS. 6 and 7 each illustrate a cross section view of a representative embodiment of the needle-tip shielding mechanism in which the mechanism comprises means for biasing the inner housing in the distal position.
Figure 7:
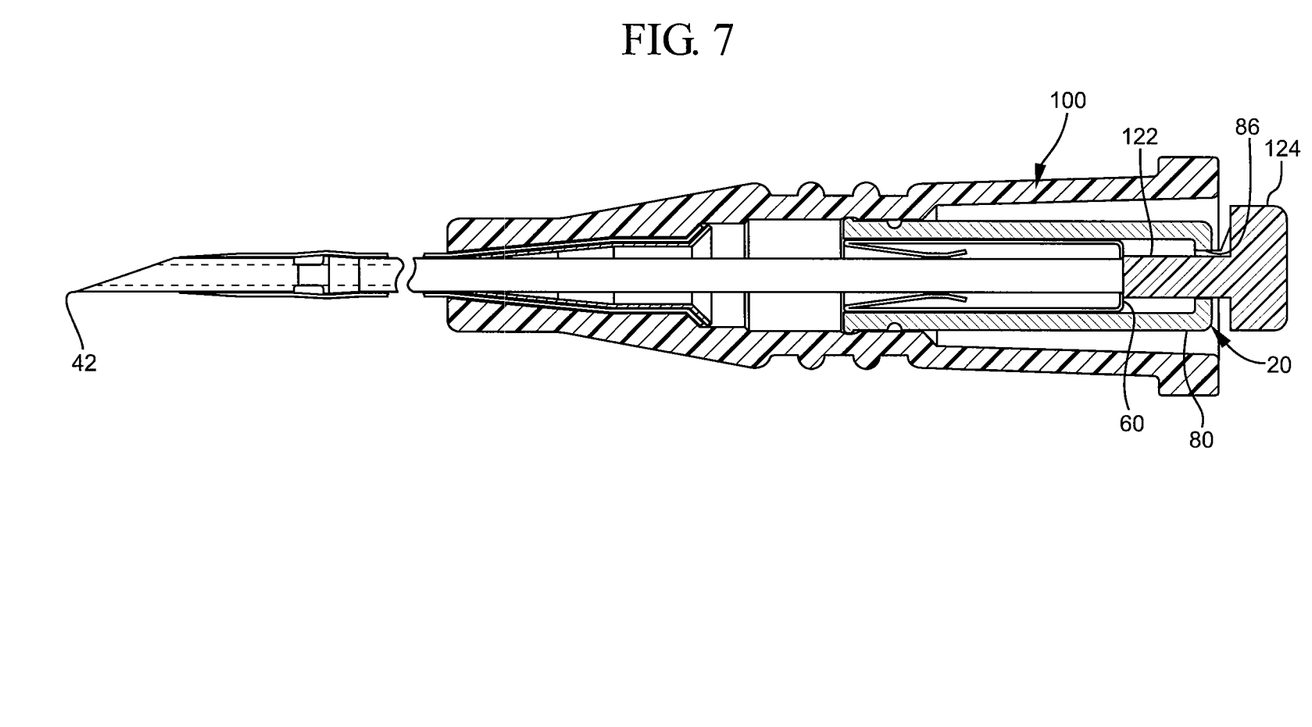

In another example, the shielding mechanism comprises means for biasing the inner housing in the distal position. In this example, the biasing means may comprise any component or characteristic that exerts a force to push or maintain the inner housing to the distal position, while still allowing the inner housing to move between the distal and the proximal position. Some examples of suitable biasing means include friction between the inner housing and the outer housing, an inner-housing detent mechanism, a needle or needle hub that is configured to bias the inner housing into the distal position, or any other component or mechanism that tends to bias the inner housing into the distal position.

Where the biasing means comprises friction between the inner housing and the outer housing, the biasing means may function in any suitable manner. For example, the outer housing may be configured (e.g., sized and shaped) so that a force (e.g., friction) between the inner housing and the outer housing is greater than the force (e.g., friction) between the inner housing and the needle until the needle feature contacts the needle-feature capture mechanism. In this example, when the needle is pulled proximally, the needle is in the unshielded position, and the inner housing is in the distal position, the needle is allowed to translate proximally into the inner housing without causing the inner housing to translate to the proximal position. However, once the needle feature's proximal engagement contacts the needle-feature capture mechanism (e.g., needle through hole 96) and the force between the needle and the inner housing is greater than the force between the inner housing and the outer housing, the inner housing is caused to translate to the proximal position (shown in FIG. 5).

Where the biasing means comprises an inner-housing detent mechanism, the detent mechanism may comprise any component that extends between the inner housing and the outer housing in a manner that can cause a force (e.g., friction) to be applied between the inner housing and the outer housing when the inner housing is moved from the distal position. For example, the inner and/or the outer housing may comprise a protuberance, an undercut, or another component that extends between the inner and outer housings and applies a force that opposes the movement of the inner housing from the distal position, wherein the force is easily overcome by an operator pulling the needle proximally. By way of illustration, FIG. 6 shows a representative embodiment in which the outer housing 80 comprises a protuberance 88 that applies a small force to the inner housing 60 when the proximal end 66 of the inner housing 60 is pulled against the protuberance 88.

Where the biasing means comprises a needle or a needle hub that is configured to bias the inner housing into the distal position, the biasing means may function in any suitable manner. In one example, the proximal opening of the outer housing is enlarged to allow a protuberant feature on the needle or the needle hub to pass distally through the proximal opening. In this example, if the inner housing is in the proximal position and the needle is pushed in the distal position, the protuberant feature passes distally through the outer housing's proximal opening, contacts the inner housing, and pushes/biases the inner housing into the distal position. In this manner, the interlock features may be moved to the engaged position. By way of illustration, FIG. 7 shows a representative embodiment in which the inner housing 60 is biased by a protuberant feature 122 on a needle hub 124 that extends through the proximal opening 86 of the outer housing 80.

Each of the described components of the shielding mechanism may be made of any suitable material. For example, the outer housing and the inner housing may be made of a medical-grade plastic, polymer, metal, metal alloy, ceramic, and/or any other suitable material. In some presently preferred embodiments, however, the outer housing comprises a plastic and the inner housing comprises a metal.

The components of the described shielding mechanism may also be made in any suitable manner. For example, the outer housing and inner housing can each be molded, stamped, pressed, cut, folded, pieced together, or otherwise be formed to their appropriate shape. In some presently preferred embodiments, however, the inner housing, including the needle-tip and needle-feature capture mechanisms, is formed from a single piece of metal (e.g., sheet metal). Additionally, in some presently preferred embodiments, the outer housing is formed through injection molding.

Figure 8:
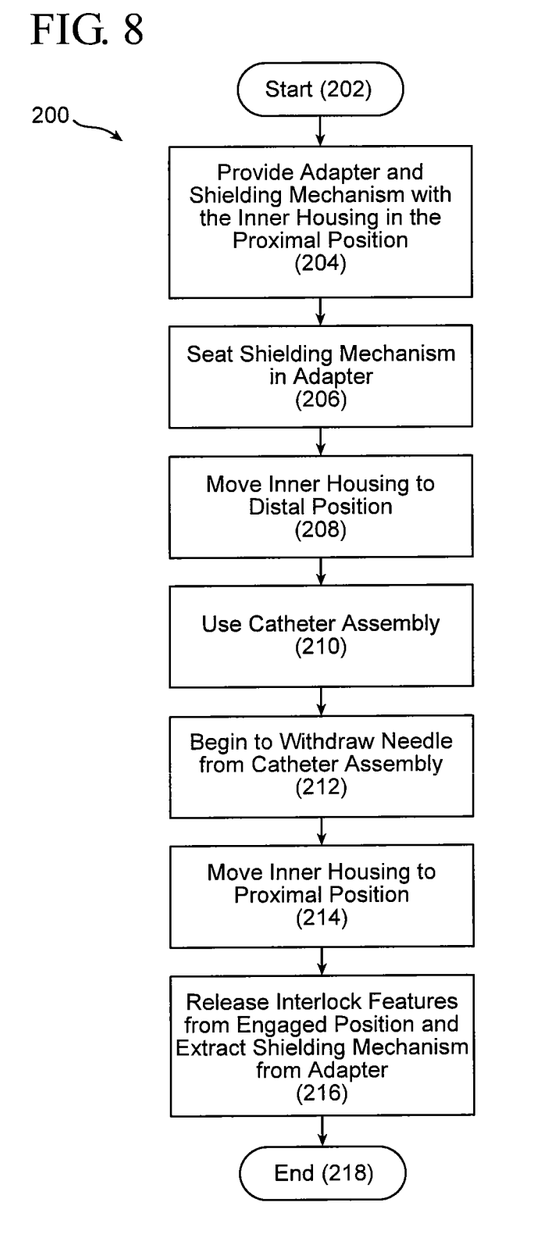
FIG. 8 is a flowchart of a representative embodiment of a method for using the shielding mechanism.

The described shielding mechanism can be used in any suitable manner. By way of example, FIG. 8 illustrates a flowchart of a representative embodiment of a method for making and using the shielding mechanism. While this method may be modified in any suitable manner, FIG. 8 shows that after beginning at box 202, the method 200 continues at box 204 by providing a catheter adapter and the shielding mechanism, with the inner housing in the proximal position. Box 206 shows the method continues as the manufacturer seats the shielding mechanism within the inner lumen of the catheter adapter. While the manufacturer may seat the shielding mechanism within the outer housing in any suitable manner, in some embodiments, the manufacturer pushes the outer housing into the adapter and until the adapter-interlock features are aligned with the corresponding interlock-feature mating components within the adapter.

Once seated, box 208 shows the method continues as the manufacturer moves the inner housing into the distal position to bias the interlock features into the engaged position. While the inner housing may be moved to the distal position in any suitable manner, in some embodiments, as discussed earlier, the manufacturer uses a protuberant feature on the needle/needle hub to push the inner housing to the distal position.

With the shielding mechanism coupled within the adapter, box 210 shows the method continues as the operator (e.g., a clinician) uses the catheter assembly by puncturing a patient's skin and blood vessel. This puncturing can be performed in any suitable manner, including through a traditional needle placement technique or a hooded technique. For example, in the traditional needle placement technique, the operator punctures the patient's skin and blood vessel with the needle and inserts the needle and catheter into the patient's blood vessel. In this example, once the catheter is properly placed within the blood vessel, box 212 shows the operator applies pressure to the blood vessel, distal to the distal tip of the catheter, and begins to withdraw the introducer needle from the catheter assembly. As the operator pulls the needle's tip proximally past the proximal-most end of the needle-tip capture mechanism (e.g., the proximal-most end 94 of the duckbilled tip barriers 92), the needle tip becomes trapped and is prevented from reemerging distally from the shielding mechanism.

Box 214 shows that as the operator continues to pull the needle proximally, the needle feature (e.g., crimp feature 54) contacts the needle-feature capture mechanism and applies a proximal force to the inner housing. As the operator continues to pull the needle and applies a force sufficient to overcome the optional biasing means, the inner housing is also pulled to the proximal position.

Figure 9:
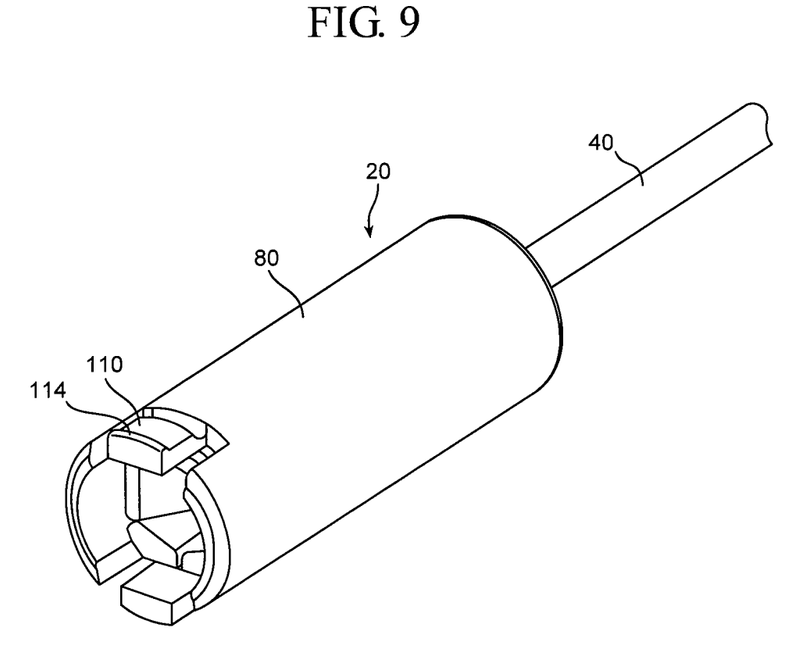
FIG. 9 illustrates a perspective view of a representative embodiment of the shielding mechanism with the needle in the shielded position.

Box 216 shows that when the inner housing is in the proximal position, the interlock features are released from the engaged position and are allowed to pivot radially inward. Accordingly, the shielding mechanism can be uncoupled from the catheter adapter in a manner that allows the shielding mechanism to be extracted from the adapter with a zero or low-force interlock release. Finally, box 218 shows the method ends as the needle and shielding mechanism are safely disposed. By way of illustration, FIG. 9 shows a representative embodiment in which the needle tip is trapped within the shielding mechanism 20 so that the shielding mechanism and the needle can be disposed.

In addition to the aforementioned benefits and advantages, the shielding mechanism may offer several additional benefits. In one example, because the shielding mechanism can be released from the adapter with little to no friction between the mechanism and the adapter (e.g., with a zero to low-force interlock release) the shielding mechanism can be released from the catheter adapter without excessive force or jerking motions, which may cause patient discomfort. In another example, the shielding mechanism has a simple design, which is inexpensive and easy to produce. In still another example, the simple design of the shielding mechanism makes the mechanism easy to use. In yet another example, the shielding mechanism can be sized to fit within the inner lumen of the catheter adapter.

The present invention may be embodied in other specific forms without departing from its structures, methods, or other essential characteristics as broadly described herein and claimed hereinafter. The described embodiments and examples are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A cannula-tip shielding mechanism, comprising:
an outer housing selectively disposed within a catheter adapter and having an adapter-interlock feature;
an inner housing comprising a cannula-feature capture mechanism and a cannula-tip capture mechanism, wherein the inner housing is slidably movable within the outer housing between a first position that biases the adapter-interlock feature into an engaged position that secures the outer housing within the catheter adapter and a second position that allows the adapter-interlock feature to move to an unengaged position thereby allowing the outer housing to be removed from the catheter adapter, the second position being proximal to the first position, and wherein, when the inner housing is in the first position, a distal end of the inner housing is contained within the outer housing; and
a cannula that extends into the inner housing, the cannula having a cannula feature.

2. The mechanism of claim 1, wherein the adapter-interlock feature comprises an arm that is pivotally connected to the outer housing.

3. The mechanism of claim 1, further comprising means for biasing the inner housing in the first position.

4. The mechanism of claim 1, further comprising an inner-housing detent mechanism.

5. The mechanism of claim 1, wherein the cannula further comprises a cannula hub having a protuberant feature that is shaped and sized to extend through a proximal opening in the outer housing and bias the inner housing into the first position.

6. The mechanism of claim 1, wherein:
the cannula-tip capture mechanism comprises a cannula tip barrier, and
the cannula-feature capture mechanism comprises a cannula through hole that is sized and shaped to allow the cannula, but not the cannula feature to pass proximally therethrough.

7. The mechanism of claim 6, wherein the inner housing is integrally formed as a single piece.

8. A catheter assembly, comprising:
a catheter adapter comprising an inner bore having an interlock-feature mating component; and
a cannula-tip shielding mechanism, comprising:
an outer housing having an adapter-interlock feature that interlocks with the interlock feature mating component;
an inner housing comprising a cannula-feature capture mechanism and a cannula-tip capture mechanism, wherein the inner housing is slidably movable within the outer housing between a first position that biases the adapter-interlock feature into an engaged position that secures the outer housing within the catheter adapter and a second position that allows the adapter-interlock feature to move to an unengaged position thereby allowing the outer housing to be removed from the catheter adapter, the second position being proximal to the first position, and wherein, when the inner housing is in the first position, a distal end of the inner housing is contained within the outer housing; and
a cannula that extends into the inner housing, the cannula having a cannula feature.

9. The catheter assembly of claim 8, wherein the adapter-interlock feature comprises an arm that is pivotally connected to the outer housing.

10. The catheter assembly of claim 8, further comprising means for biasing the inner housing in the first position.

11. The catheter assembly of claim 8, further comprising an inner-housing detent mechanism that biases the inner housing in the first position.

12. The catheter assembly of claim 8, wherein the cannula further comprises a cannula hub having a protuberant feature that extends through a proximal opening in the outer housing and biases the inner housing into the first position.

13. The catheter assembly of claim 8, wherein:
    the cannula-tip capture mechanism comprises a cannula tip barrier, and
    the cannula-feature capture mechanism comprises a cannula through hole.

14. A method for using a cannula-tip shielding mechanism, the method comprising:
    providing a cannula-tip shielding mechanism comprising:
        an outer housing having an adapter-interlock feature for securing the outer housing within an adapter;
        an inner housing comprising a cannula-feature capture mechanism and a cannula-tip capture mechanism, wherein the inner housing is slidably movable within the outer housing between a first position that biases the adapter-interlock feature into an engaged position that secures the outer housing within the adapter and a second position that allows the adapter-interlock feature to move to an unengaged position thereby allowing the outer housing to be removed from the adapter, the second position being proximal to the first position, and wherein, when the inner housing is in the first position, a distal end of the inner housing is contained within the outer housing; and
        a cannula that extends into the inner housing, the cannula having a cannula feature; and
    moving the inner housing to the second position.

15. The method of claim 14, further comprising moving the inner housing to the first position.

16. The method of claim 15, comprising moving the inner housing by pushing the inner housing with a protuberant feature on a surface selected from a cannula hub and a cannula outer surface, wherein the protuberant feature passes through a proximal opening on the outer housing.

17. The method of claim 14, wherein the adapter-interlock feature comprises an arm that is pivotally connected to the outer housing.

18. The method of claim 14, wherein the cannula-tip shielding mechanism further comprises an inner-housing detent mechanism that biases the inner housing in the first position.

19. The method of claim 14, wherein:
    the cannula-tip capture mechanism comprises a cannula tip barrier, and
    the cannula-feature capture mechanism comprises a cannula through hole.

* * * * *